United States Patent [19]
Dorian

[11] 4,109,384
[45] Aug. 29, 1978

[54] DENTAL TOOLS

[76] Inventor: Hubert J. Dorian, 10527 Leconte Ave., Los Angeles, Calif. 90024

[21] Appl. No.: 848,765

[22] Filed: Nov. 4, 1977

Related U.S. Application Data

[63] Continuation of Ser. No. 593,225, Jul. 7, 1975, abandoned.

[51] Int. Cl.² ............................................. A61C 3/02
[52] U.S. Cl. ...................................... 32/40 R; 32/46
[58] Field of Search .................... 32/40 R, 50, 48, 46, 32/47, 51; 30/344; 228/132

[56] References Cited

U.S. PATENT DOCUMENTS

| | | | |
|---|---|---|---|
| 550,508 | 11/1895 | How | 32/50 |
| 794,591 | 7/1905 | Decherd | 30/344 |
| 1,872,022 | 8/1932 | White | 228/132 |
| 3,562,912 | 2/1971 | Edelman | 32/40 R |

*Primary Examiner*—Robert Peshock
*Attorney, Agent, or Firm*—Robert J. Schapp

[57] ABSTRACT

A dental tool assembly for performing dental work on the teeth or restorations in the oral cavity of a human being. The dental tool assembly comprises a handle having an elongated hand-grip portion. The hand-grip portion is provided with an aperture in one end thereof to receive a dental tool portion. The dental tool portion is provided with a securement end extendible into the aperture and a working end on the opposite end of the dental tool portion. The securement end of the dental tool portion is inserted in the aperture and, in one embodiment, is soldered therein so that it is retentively held onto the handle. After a period of use, the tool portion of the assembly may be removed by merely heating the joint area between the hand-grip and the tool. In another embodiment of the invention, the securement end of the dental tool portion is threadedly secured in the aperture of the hand-grip portion. In a preferred aspect of the present invention, the tool is provided with a tooth or restoration contact end which is uniquely sized and shaped in order to aid in the efficiency of performing dental work in the oral cavity.

16 Claims, 17 Drawing Figures

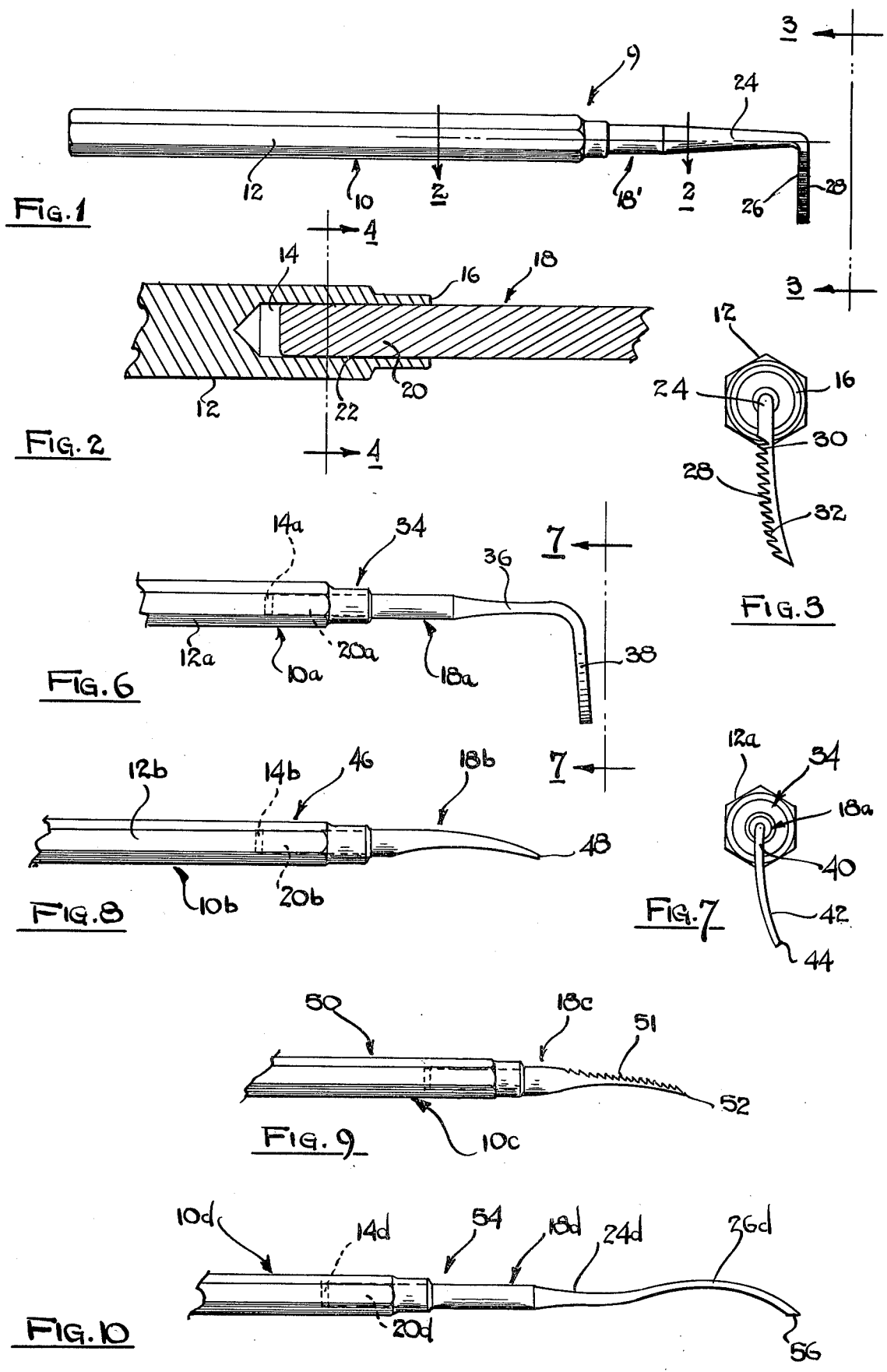

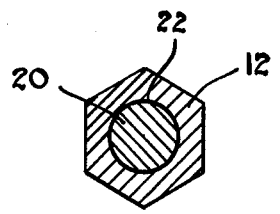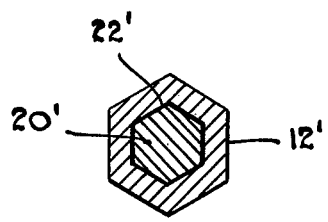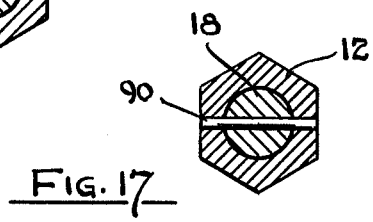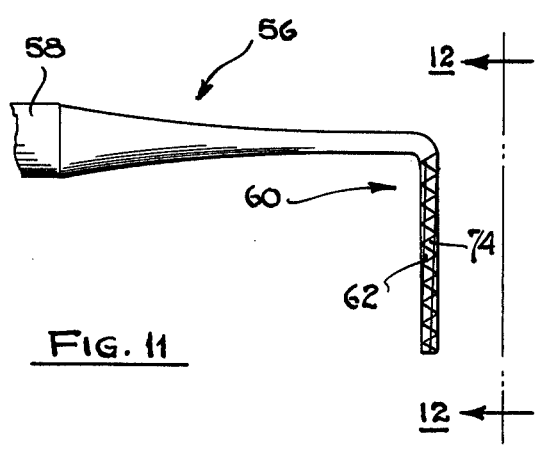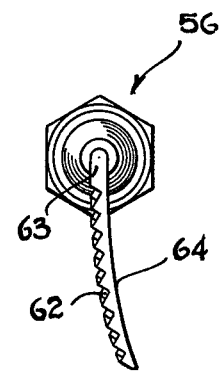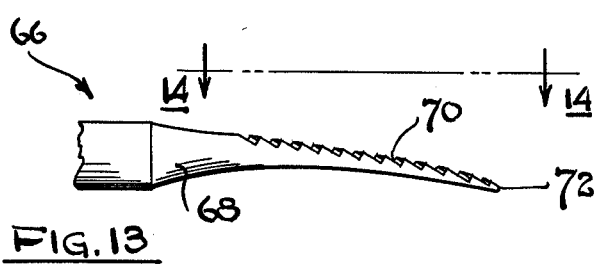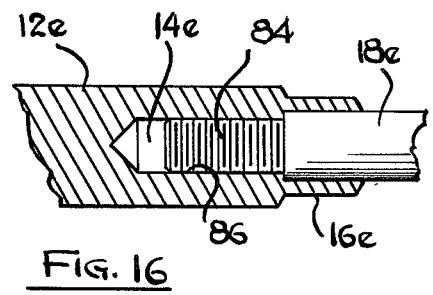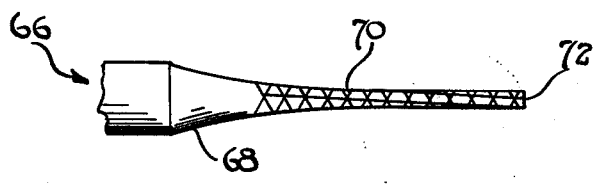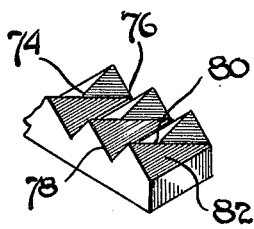

DENTAL TOOLS

This application is a continuation application of the commonly owned, copending patent application for "DENTAL TOOLS" bearing Ser. No. 593,225, filed July 7, 1975, and which has been abandoned.

BACKGROUND OF THE INVENTION

This invention relates in general to certain new and useful improvements in dental tool assemblies and, more particularly, to dental tool assemblies including a handle portion and a removable tool portion.

For a long period of time, the art of hand-operable dental tools has not materially changed. Generally, these dental tools include a hand-grip portion as well as a tool end which is fabricated to perform a particular function. These dental tools are typically only used by a dentist and adopt a variety of forms, as for example, an interproximal file, an interproximal chisel, and the like. Nevertheless, these tools are generally formed of a relatively expensive tempered steel and machined to desired tolerances.

Due to the materials of construction, and the rather substantial cost in the fabrication of such tools, it can be readily understood that these tools are quite expensive. Moreover, each dentist is requird to maintain a large number of the tools since similar tools must be provided in varying sizes. In addition, a right-hand tool and a left-hand tool must be provided for each size. Furthermore, as indicated above, the tools occur in a larger number of constructions, as for example a file or a blade or a chisel, or the like. Consequently, the average dentist is required to carry an inventory of a large number of these various dental tools.

Notwithstanding the high cost of the tools and when considering the large number required to be maintained in each dental office, and which hence constitute a large capital outlay, these tools are only effective for a relatively short period of time inasmuch as the dentist must often apply a degree of manual pressure in order to accomplish the desired end result in the oral cavity. Therefore, the contact end portion of the tool assembly either tends to become worn, and thereby inefficient, or otherwise the tool does often break which requires the purchase of a new tool.

It is therefore the primary object of the present invention to provide a dental tool assembly comprising a hand-grip portion and a tool portion where the tool portion is removably attached to the hand-grip portion.

It is another object of the present invention to provide a dental tool assembly of the type stated which is highly efficient in its operation and can be constructed at a relatively low unit cost.

It is a further object of the present invention to provide a dental tool assembly of the type stated in which the tool portion has a contact end uniquely designed to accomplish a particular result on the teeth or restorations in the oral cavity.

It is a further object of the present invention to provide a dental tool assembly of the type stated which includes a hand-grip portion and a tool portion where the hand-grip portion is designned to accommodate a wide variety of tool portions of various sizes and shapes.

It is also an object of the present invention to provide a method of extending the normal life of a dental tool used in dental work on the teeth and restorations in an oral cavity by employing a hand-grip portion and a removable tool portion.

With the above and other objects in view, my invention resides in the novel features of form, construction, arrangement and combination of parts presently described and pointed out in the claims.

SUMMARY OF THE DISCLOSURE

The present invention relates to a dental tool assembly which is capable of being manually operable for performing dental work on the teeth or restorations in the oral cavity of a human being. This tool assembly includes a handle section having an elongated hand-grip portion in which the hand-grip portion is provided with an aperture in one end thereof. The tool assembly also includes a section having a securement end which is capable of being inserted in the aperture of the hand-grip portion. The tool portion also is provided with a working end opposite the securement end and where the securement end is provided with the size and shape to fit within the aperture. A securement means is designed to retentively, but nevertheless removably, hold the securement end of the tool portion within the hand-grip portion.

In further detail, the securement means, in one embodiment of the invention, is essentially a heat-responsive solder material. In this way, the solder can be inserted between the wall of the aperture in the handle section and the securement end of the tool so that the tool is retentively held within the aperture, although, upon application of heat, the tool can be removed through the melting of the solder. A guide pin means can also be used to properly locate the tool portion with respect to the hand-grip portion.

In another embodiment of the invention, the aperture in the hand-grip portion could be provided with internal screw-type threads. In addition, the securement end of the tool portion would be provided with mating external threads so that the tool portion could be threadedly secured to the hand-grip portion.

The dental tool of the present invention is also present in a wide variety of tool forms, as for example, an interproximal file, an interproximal chisel and the like. Nevertheless, each of these tools is unique in that they are specifically designed to be more efficient and effective in accomplishing the intended end result. Each of the tools is provided with a contact section for contacting and working on the teeth and restorations in the oral cavity. Moreover, these-various tools are unique in their sizes and shapes as hereinafter described.

The present invention also provides a method of extending the life of the dental tool used in the dental work on the teeth and restoration in the oral cavity. This method comprises the provision of a handle assembly with a hand-grip portion having an aperture in one transverse end. The method also provides for the insertion of the securement end of the tool into the aperture of the hand-grip and also inserting a heat-responsive metal composition between the wall of the aperture and the external surface of the securement end. In this way, it is possible to allow this composition to harden and thereby removably secure the work tool to the hand-grip portion.

The working ends of the tools of the present invention are also uniquely designed, with respect to the prior art, in order to facilitate the performance of the required dental function in the oral cavity of a patient. These working ends are uniquely shaped and located at desired angles as hereinafter described in more detail. In addition, one of these working ends in the form of an interproximal chisel is provided with a cross-cut contact surface which has been found to be highly efficient.

In many cases, these dental tools are referred to as "dental instruments", although the termns are used synonymously and, accordingly, the term "dental tool" as used herein is synonymous with the term "dental instrument".

BRIEF DESCRIPTION OF THE DRAWINGS

Having thus described the invention in general terms, reference will now be made to the accompanying drawings in which:

FIG. 1 is a side-elevational view of a dental tool assembly constructed in accordance with and embodying the present invention;

FIG. 2 is a fragmentary sectional view taken along line 2—2 of FIG. 1, and showing the means of attaching a tool section to a hand-grip section forming part of the tool assembly of the present invention;

FIG. 3 is an enlarged end-elevational view, substantially taken along line 3—3 of FIG. 2, and showing one embodiment of the tool assembly in the form of an interproximal file;

FIG. 4 is a vertical sectional view taken along line 4—4 of FIG. 2;

FIG. 5 is a vertical sectional view similar to FIG. 4 and showing a modified form of tool assembly construction in accordance with the present invention;

FIG. 6 is a side-elevational view showing a modified form of the tool assembly of the present invention in the form of an interproximal blade;

FIG. 7 is an end-elevational view substantially taken along line 7—7 of FIG. 5;

FIG. 8 is a fragmentary side-elevational view showing another modified form of dental tool assembly of the present invention showing another form of an interproximal blade;

FIG. 9 is a fragmentary side-elevational view substantially similar to FIG. 8, and showing the dental tool assemby in the form of a modified interproximal file;

FIG. 10 is a fragmentary side-elevational view, substantially similar to FIG. 9, and showing the dental tool assembly in the form of an interproximal chisel;

FIG. 11 is a fragmentary side elevational view of a modified form interproximal file, similar to that of FIG. 2;

FIG. 12 is a fragmentary side elevational view of the file of FIG. 11, taken substantially along the plane of line 12—12 of FIG. 11;

FIG. 13 is a fragmentary side elevational view of a modified form of another interproximal file, similar to that of FIG. 9;

FIG. 14 is a fragmentary top plan view of the file of FIG. 13, taken substantially along the plane of the line 14—14 of FIG. 13;

FIG. 15 is a fragmentary enlarged perspective view showing a portion of the cutting teeth in the files of FIGS. 11-14;

FIG. 16 is a fragmentary vertical sectional view similar to FIG. 2 and showing a modified form of attaching a tool section to a handle section; and FIG. 17 is a fragmentary vertical transverse sectional view showing still a further modified form of attaching a tool section to a handle section.

DETAILED DESCRIPTION

Referring now in more detail and by reference characters to the drawings, reference numeral 9 designates a dental tool assembly which is constructed in accordance with and embodies the present invention. The dental tool assembly 9 generally comprises a handle section or so-called "handle" 10 having a hand-grip portion 12 which is generally non-cylindrical in shape. The handle section 10 is provided with an aperture 14 formed in a relatively flat transverse end 16 thereof.

Also provided for the dental tool assembly 9 of the present invention is a tool section or so-called "tool" 18 having a securement end 20 which is sized and shaped for disposition within the aperture 16. Moreover, the securement end 20 is retentively secured within the aperture 14 by means of a heat solderer illustrated at reference numeral 22. In this way, it can be observed that the tool section 18 is retentively secured within the handle section 10. Thus, it can be observed that by insertng the securement end 18 within the aperture 14 and applying a solder material thereto, the tool section 18 can be retentively held with respective to the handle section 10. Moreover, in the event that it is desired to remove the tool section 18, it is merely necessary to apply heat in order to melt the solder material and thereby release and remove the tool section 18.

One of the unique aspects of the present invention is that it has been found that solder, that is the conventional tungsten containing solder, is a highly effective means of removably attaching the tool section 18 to the handle section 10. A highly effective threaded attachment means is also described hereinafter in more detail. While other forms of attachment means could be envisioned, these other forms of attachment means are not nearly as effective as the use of securing the tool section 18 to the handle section 10 by means of solder, or by the aforesaid threaded attachment.

One of the unique aspects of using solder is that it is oftentimes desirable to provide the securement end 20 with a circular cross section as illustrated in FIG. 4 of the drawings, and in this case, the aperture 14 would also have a circular cross section. Consequently, other forms of attachment means are thereby rendered relatively ineffective. Notwithstanding, it should be also understood that the securement end 20 could have a non-cylindical shape, as designated by reference numeral 20' in FIG. 5 of the drawings. In like manner, the aperture 14 would also be non-cylindrically shaped and in this case the securement end 20 of the tool section 18 would be secured by a soldering bonding 22'. While the securement end 20' and the aperture formed in the handle section 12' is illustrated as a heptagon, it should be understood that any form of non-cylindical section could also be utilized.

The dental tool assembly 9, which is illustrated in FIGS. 1-4 of the drawings and the embodiment of FIG. 5 thereof, is illustrated in the form of an interproximal file which includes a retaining leg 24 substantially coaxial with the handle section 10 and a contact end portion 26 which is generally perpendicular to the retaining arm 24. In this case, the contact end section 26 includes a file section 28 for performing work on the teeth or restorations in the oral cavity. One of the important aspects of the contact end section 26 is that it is generally perpendicularly located to the retaining arm 24. By reference to FIG. 3 of the drawings, it can be observed that the contact end section 28 includes a relatively straight portion 30 and arcuate portion 32. In this case, the arcuate portion is essentially non-circular, that is, it does not have a truly circular arc. However, it should be understood in accordance with the present invention that the arcuate portion 32 could have, as in many cases, a circular arcuate portion. In this case, it can be observed that the relatively straight portion 30 is relatively short in length when compared to the arcuate section 32. It has been found that this form of construction is significantly more advantageous in performing interproximal work in the oral cavity of the human being.

FIG. 6 illustrates a modified form of dental tool assembly 34 constructed in accordance with and embodying the present invention, and which includes a handle section 10a having a hand-grip portion 12a which is also generally non-cylindrical on its external surface. In like manner, the handle section 10a is provided with an aperture 14a similar to the aperture 14 in one relatively flat transverse end thereof. A dental tool assembly 18a is provided for securement to the handle section 10a and includes a securement end 20a which is inserted in the aperture 14a. In addition, the securement end 20a is also retentively heat-soldered in the aperture 14a.

The dental tool assembly 34 of the present invention adopts the form of an interproximal blade which includes a retaining arm 36 substantially coaxial with the aperture 14a and a work or contact end 38 generally located in perpendicular relationship to the retaining arm 36. In this case, the contact portion 38 also includes a relatively straight section 40 and an arcuate section 42. The arcuate section 42 is similar to the arcuate section 32 in that it does not have a non-circular arcuate portion. Although, in some constructions, this arcuate portion 42 would include at least a portion of a truly cylindrical arc. However, it is also to be noted in accordance with FIGS. 6 and 7 of the drawings that the arcuate section 42 terminates in somewhat of an oblique edge 44.

FIG. 8 illustrates another form of dental tool assembly, designated by reference numeral 46, and which is also constructed in accordance with and embodies the present invention. In this case, the dental assembly 46 includes a handle section 10b having a non-cylindrically shaped hand-grip 12b. In addition, the handle section 10b is provided with an aperture 14b in one transverse end thereof. Secured to the handle section 10b is a tool section 18b which has a securement end 20b sized and shaped for disposition in the aperture 15b. In addition, this tool section 18b adopts the form of an interproximal blade, somewhat similar to the tool section 18a. Nevertheless, this interproximal blade 18b is essentially arcuate on its upper surface and is provided with an arcuate undersurface terminating in a relatively sharp point 48. In this case, it can be observed that the upper surface and the lower surface of the blade forming part of the tool 18b, while preferably being defined by non-circular arcs, could also be defined by circular arcs. Nevertheless, the tool section 18b is also essentially somewhat rectangular in vertical cross section.

FIG. 9 illustrates another modified form of dental tool assembly 50 constructed in accordance with and embodying the present invention and which includes a handle section 10c and a tool section 18c. In this case, the tool section 18c is similar to the tool section 18b, as illustrated in FIG. 8 of the drawings, but nevertheless includes a file portion 51 on one surface thereof. Otherwise, the dental tool assembly 51 is similar to the dental tool assembly 46. Moreover, it can be observed that the tool section 18c terminates in a relatively sharp point 52.

FIG. 10 illustrates another modified form of dental tool assembly 54 constructed in accordance with and embodying the present invention and which includes a handle section 10d and a tool section 18d. The tool section 18d is similarly provided with a securement end 20d which extends into and is retentively held within an aperture 14d provided in one transverse end of the handle section 10d. In this case, it can be observed that the tool section 18d adopts the form of an interproximal chisel including a relatively straight section 24d terminating in an arcuate contact end section 26d. Moreover, the arcuate contact end 26d terminates in a chisel point 56 in the manner as illustrated in FIG. 10 of the drawings. In this case, it can be observed that the chisel point has an edge lying in a plane which is somewhat parallel to the axial centerline of the aperture 14d.

In accordance with the above, it can be observed that the various dental tool assemblies described herein are only a limited number of dental tool assemblies which could be utilized in accordance with the present invention. These dental tool assemblies all include a handle section and a removable, but nevertheless retentively held, tool section. One of the unique aspects of the present invention is that it has been found that the tool section can be retentively, although nevertheless removably, held within the handle section by means of a solder joint. This solder joint is highly unique in that it enables the interchangeability of other forms of tool sections with respect to an individual handle section by merely heating the solder joint to remove one tool section and replacing another tool in the handle section with additional solder. Moreover, the use of solder as a means of retaining the tool section within the handle section has been found to be far superior to any other form of retaining means, except for the threaded attachment means, inasmuch as it provides the necessary rigidity without otherwise obstructing the work normally accomplished by the dentist.

FIGS. 11 and 12 of the drawings illustrate a modified form of an interproximal file 56 which includes a retaining leg 58 substantially coaxial with and secured to a handle section, such as the handle section 10, as previously described, and a contact end portion 60 which is generally perpendicular to the retaining leg 58. In this case, the contact end portion 60 includes a file section 62 for performing work on the teeth or restorations or bone in the oral cavity. The contact end section 60 is generally perpendicularly located to the retaining leg 58. By reference to FIG. 12 of the drawings, it can be observed that the contact end section 60 includes a relatively straight portion 63 and an arcuate portion 64 which also is essentially non-circular, that is, it does not have a truly circular arc. Again, the arcuate portion 64 could have a circular arcuate portion and, moreover, the relatively straight portion 63 is relatively short in length when compared to the arcuate section 64.

FIGS. 13 and 14 illustrate another modified form of dental tool assembly 66 in the form of a further modified form of interproximal file constructed in accordance with and embodying the present invention, and which includes a tool section 68 similar to the tool section 18c. In this case, the tool section 68 includes a file 70 on one surface thereof and which terminates in a relatively sharp point 72.

With respect to the file sections 62 and 70 of the interproximal files 56 and 66, respectively, these file sections have so-called "cross-cut" teeth in the same manner as a cross-cut saw. In this way, it is possible to create a filing action in the oral cavity in a reciprocative manner as opposed to moving the file in one direction, lifting the same from the surface of the oral cavity, moving back to an original position and then moving the file on the surface of the oral cavity in one direction. Heretofore, it was believed that filing action could only be performed in one direction of movement of the file. Nevertheless, it has been found that the files of the present invention are highly effective for filing action in both directions of a reciprocative movement with the cross-cut teeth. Moreover, by using such files, it has been found that such work can be performed in about one-half the normal time previously required, thus affording significant advantages to both the patient and the dentist.

FIG. 15 more fully illustrates the form of file section which is used in a preferred aspect of the interproximal files of FIGS. 11–14. In this case, it can be observed that the file section 70 includes one elongate central groove 74 and a series of diagonally cross-cut grooves 76 and 78 which form inclined triangular sections 80. Each of these triangular sections 80 have a frontal cutting surface 82, in the manner as illustrated in FIG. 15 of the drawings. This form of file section 70 is similar to the so-called rasp bastard cut normally found in rasp bastard files. However, it should be observed that double cut file sections, or single cut file sections, including both coarse and bastard sections, could also be employed.

This form of file section has been found to be the most effective in accordance with the present invention, although it should be understood that other forms of cross-cut file arrangements could be used.

FIG. 16 illustrates a further modified form of the dental tool of the present invention, and which includes a handle 10e having a hand-grip portion 12e which is generally non-cylindrical in shape and which is also provided with an aperture or central-bore 14e formed in a tranverse end 16e thereof. Also provided for the dental tool assembly, as illustrated in FIG. 16, is a tool section 18e having an externally threaded inner end 84 which mates with and is threadedly secured to a generally threaded section 86 in the aperture 14e. In this way, the tool section 18e may be threadedly secured within the aperture 14e. Moreover, the mating threads 84 and 86 are so designed so that when the tool section 18e is inserted in the aperture 14e, it can be rotated to a precise position so that the contact end (not shown) of the tool section 18e is precisely aligned with respect to the hand-grip portion 12e.

It has been found in connection with the present invention, that the use of the threaded securement end is equally as effective as the soldered securement means as described above and offers all of the advantages of the soldered securement means described above. Moreover, with respect to the threaded securement end, it is possible for a dentist, or like user of the dental tool of the present invention, to merely remove the tool section from the handle section and insert a new tool section without the necessity of engaging in a heat soldering or like technique.

FIG. 17 illustrates a further embodiment of the present invention and which is similar to the embodiment illustrated in FIGS. 1 and 2 of the drawings. In this case, it can be observed that the tool section 18 is also provided with a securement end 20 which is also circular in shape and which fits within a circular aperture 14. However, in this case, the handle section 10 and the tool section 18 are provided with transversely aligned bores in order to accommodate a guiding pin 90 which may also be threadedly secured within the transversely aligned bores. In this way, it is possible to precisely locate the tool section 18 with respect to the hand-grip portion 12 on the handle section 10. Moreover, the pin 90 is threadedly secured within this bore and may be easily removable therefrom in order to interchange tool sections therefor.

Thus, there has been illustrated and described a unique and novel dental tool assembly and a method of using and providing the same and which therefore meets and fulfills all of the objects and advantages sought therefor. It should be understood that many changes, modifications, variations and other uses and applications may become apparent to those skilled in the art after considering the specification and the accompanying drawings. Therefore, any and all such changes, modifications, variations and other uses and applications are deemed to be covered by the invention which is limited only by the following claims.

in thus described my invention is general terms, what I desire to claim and secure by letters patent is:

1. A dental tool assembly for performing dental work on the teeth or restorations in the oral cavity of a human being, said tool assembly comprising a handle assembly have an elongated hand-grip portion, said hand-grip portion having a recess formed on one transverse end thereof, a replaceable tool section having a securement end and a working end opposite said securement end, said working end having a contact section sized and shaped to perform dental work on the teeth or restoration in the oval cavity of a human being, said hand-grip portion having said recesses defined by an interior wall and an end wall, said securement end having an extension with an outer surface with a size and shape to fit within and which is closely spaced to the interior wall of said recess, and said extension having an end wall spaced from the end wall of said recess to form a space therebetween, and a heat responsive solder material securement means to retentively, but nevertheless removably, hold the extension on the securement end of said tool section within the recess of said hand-grip portion, said solder material being comprised of a tin-lead alloy composition and essentially surrounding the outer surface of said securement end and bonding the extension on the securement end to the interior wall of said aperature upon heating to a temperature where the composition liquifies and thereafter hardens upon cooling to create a metal bond between the interior wall and said securement end, but which solder material is capable of releasing said securement end on heating of the same to a temperature where the composition liquifies, said composition being applied in such amount that all said composition remains entirely within said recess and any excess thereof being disposed in said space.

2. The dental tool assembly of claim 1 further characterized in that said recess in said hand-grip portion is essentially cylindrically shaped and that the securement end of said tool section is also cylindrically shaped, said hand-grip portion in the region of said recess and said extension on said securement end having aligned openings which also receive a removabele locking pin.

3. The dental tool assembly of claim 1 further characterized in that said recess in said hand-grip portion if essentially non-cylindrically shaped and that the extension on said securement end of said tool section is also non-cylindrically shaped, said hand-grip portion in the region of said recess and said extension on said securement end having aligned openings which also receive a removable locking pin.

4. The dental tool assembly of claim 1 further characterized in that said end contact section comprises a relatively straight section and an arcurate section.

5. The dental tool assembly of claim 4 further characterized in that said arcuate section is defined by a non-circular arc.

6. The dental tool assembly of claim 4 further characterized in that said tool assembly is an interproximal file and said straight section has a length which is relatively short compared to said arcuate section.

7. The dental tool assembly of claim 1 further characterized in that said contact section is somewhat rectangularly shaped in cross section.

8. The dental tool assembly of claim 5 further characterized in that said arcuate section has a cylindrically shaped arc along a portion thereof.

9. The dental tool assembly of claim 1 further characterized in that said tool section is an interproximal device and that said tool has a straight section generally coaxial with said handle and an end contact section for engaging the teeth and restorations and which contact section is substantially perpendicular with respect to said straight section.

10. The dental tool assembly of claim 9 further characterized in that said contact section is relatively rectangular in cross section.

11. The dental interpoximal file of claim 6, said file having cross-cut teeth thereon, said cross-cut teeth being formed by a plurality of upstanding ridges being in turn formed by a plurality of spaced apart diagonally extending grooves and an elongate central groove essentially perpendicular to said plurality of spaced apart grooves to thereby form a plurality of triangular teeth sections, at least certain of said teeth sections having a frontal cutting edge and at least certain of said teeth sections having a rearward cutting edge to constitute said cross-cut teeth.

12. A method of extending the life of a dental tool used in dental work on teeth and restorations in the oral cavity, said method comprising providing a handle assembly having a hand-grip portion with a recess defined by an interior wall on an inner end wall formed in one transverse end thereof, inserting an extension extending outwardly from a securement end of a replaceable dental tool in said recess and which extension on said securement end has an exterior surface closely spaced to the interior wall of said recess and an end wall spaced from the end wall of said recess to form a space therebetween, said work tool having a contact section on an end opposite said securement end and which contact section is sized and shaped to perform dental work on the teeth or restoration in the oval cavity of a human being inserting a heat-responsive solder composition comprised of a tin and lead alloy between the interior wall of said recess and the external surface of said extension on said securement end, heating said composition to a temperature where it liquifies and thereafter permitting said composition to cool when said securement end is in said recess to allow said composition to harden and thereby removably secure said work tool to said hand-grip portion with any excess of said composition being returned within said space, and said solder composition capable of being liquified upon heating to enable removal of said work tool.

13. The method of claim 12 further characterized in that said method comprises removing said work tool by hearing the extension on the securement end of said work tool and the interior wall of said recess to liquify said solder composition.

14. The method of claim 12 further characterized in that said tools has a retaining section and work section.

15. A dental tool assembly for performing dental work on the teeth or restorations in the oral cavity of a human being, said tool assembly comprising a handle assembly having an elongated hand-grip portion, said hand-grip portion having a recess formed on one transverse end thereof, a replaceable tool section having a securement end and a working end opposite said securement end, said hand-grip portion having a recess located in one transverse end thereof and being defined by an interior wall and an end wall, said securement end having an extension with an outer surface with a size and shape to fit within and which is closely spaced to the interior wall of said recess and said extension having an end wall spaced from the end wall of said recess to form a space therebetween, and a heat responsive solder material securement means comprised of a tin-lead alloy to retentively, but nevertheless removably, hold the extension on the securement end of said tool section within the recess of said hand-grip portion, said solder material essentially surrounding the outer surface of said extension on said securement end and bonding the extension on the securement end to the interior wall of said recess with an excess of said solder material being contained within said space but which solder material is capable of releasing said extension on said securement end on heating of the same, said working end having a contact section which is capable of engaging a portion of the oral cavity, a file portion on said contact section and having cross-cut teeth thereon, said cross-cut teeth being formed by a plurality of upstanding ridges extending somewhat diagonally on said contact section, said ridges being in turn formed by a plurality of spaced apart diagonally extending grooves and an elongate central groove essentially perpendicular to said plurality of spaced apart grooves to thereby form a plurality of triangular teeth sections, at least certain of said teeth sections having a frontal cutting edge and at least certain of said teeth sections have a rearward cutting edge to constitute said cross-cut teeth.

16. The dental interproximal file of claim 15 further characterized in that said end contact section comprises a relatively straight section and an arcuate section.

* * * * *